United States Patent [19]

Miner et al.

[11] Patent Number: 5,342,536
[45] Date of Patent: Aug. 30, 1994

[54] NAIL POLISH REMOVER WITH GELATIN

[75] Inventors: Philip E. Miner, Newtown; Walter Rose, New Haven, both of Conn.

[73] Assignee: Chesebrough-Pond's USA Co., Division of Conopco, Inc., Greenwich, Conn.

[21] Appl. No.: 992,513

[22] Filed: Dec. 17, 1992

[51] Int. Cl.$^5$ .................. C09D 9/00; B08B 7/00
[52] U.S. Cl. ....................... 252/162; 252/153; 252/170; 252/171; 252/DIG. 8; 134/38; 134/39
[58] Field of Search ............. 424/61; 252/162, 170, 252/DIG. 8; 134/38, 39

[56] References Cited

U.S. PATENT DOCUMENTS

| | | | |
|---|---|---|---|
| 3,729,569 | 4/1973 | Charle et al. | 424/14 |
| 4,735,798 | 4/1988 | Bernstein | 424/61 |
| 4,897,261 | 1/1990 | Yamazaki | 424/61 |

*Primary Examiner*—Paul Lieberman
*Assistant Examiner*—Necholus Ogden
*Attorney, Agent, or Firm*—Milton L. Honig

[57] ABSTRACT

A nail polish or lacquer removing composition is provided that includes a volatile organic solvent such as acetone, gelatin and glycerin present to stably suspend the gelatin in the solvent.

5 Claims, No Drawings

NAIL POLISH REMOVER WITH GELATIN

BACKGROUND OF THE INVENTION

1. Field of the Invention

The invention relates to the suspension of gelatin in nail polish remover.

2. The Related Art

Products have long been marketed for the removal of nail polish (lacquer) from fingernails and toenails. Essentially, these products consist of a solvent(s) with which to dissolve the lacquer. Typically, the solvent will be a relatively volatile material such as acetone or ethyl acetate.

Organic solvents have a tendency to remove natural emollients found in the nail. As a result, nails become brittle.

There have been reported attempts to overcome the adverse effects of solvents on fingernails and surrounding skin. For instance, U.S. Pat. No. 4,032,464 (Mausner) reports a nail lacquer remover in a creamy viscous form that minimizes the danger of skin irritation. The composition is an aqueous solution that includes a chelating agent, a humectant such as propylene glycol, 2-hydroxy-4-methoxy-benzophenone-5-sulfonic acid, a proteinaceous material and palmitates of Vitamins A and D alongside a carboxy vinyl polymer thickener.

U.S. Pat. No. 4,735,798 (Bernstein) is a further example of the art. Therein a nail polish remover composition is reported comprising a mixture of acetone, ethyl acetate ethyl alcohol, water and glycerin (glycerol). The composition was indicated to have disinfectant properties, strengthen the fingernails and have a pleasant feel while allowing subsequent coatings of nail polish to adhere better.

Co-pending U.S. patent application Ser. No. 07/945,428 to Remz et al describes a lacquer removing composition that includes acetone, water, glycerin and a conditioning agent such as $C_8$-$C_{20}$ fatty acid derivative held in suspension by an acrylic copolymer. The commercial embodiment of the composition mentioned in this application is found in Cutex Polish Remover with Vaseline Intensive Care ® lotion.

Gelatin has long been known as a nail strengthening ingredient. Indeed, many commerically available lacquer removers have included gelatin as a component. A problem with gelatin in acetone and water systems is that of maintaining insoluble gelatin in suspension under long term storage conditions.

Accordingly, it is an object of the present invention to provide a nail polish remover that includes gelatin in a stably suspended state even after prolonged storage.

A further object of the present invention is to provide a nail polish remover which will ameliorate the problem of nail embrittlement caused by solvent stripping.

These and other objects of the present invention will become more readily apparent through the detailed description of the invention and examples that follow.

SUMMARY OF THE INVENTION

A nail polish removing composition is provided comprising:
 (i) from about 50% to about 99.5% of a volatile organic solvent;
 (ii) from about 0.00001% to about 5% by weight of gelatin; and
 (iii) from about 0.1% to about 10% by weight of glycerin.

DETAILED DESCRIPTION OF THE INVENTION

The present invention provides compositions that include a major amount of volatile organic solvent in combination with gelatin. Now it has been discovered that the gelatin can be stably suspended with the aid of glycerin.

Volatile organic solvents employed for the present invention will have a boiling point lower than 100° C., preferably below 50° C. Acetone, ethyl acetate, ethyl alcohol, methyl alcohol, isopropyl alcohol and methyl ethyl ketone are the solvents of choice. Amount of the solvent will range from about 50% to about 99.5% by weight of the total composition. Preferably, the amount will range from about 75% to about 90%, optimally, about 85% by weight.

Water may also be present in the compositions. Amounts of water may range anywhere from 0.01% up to about 25%, preferably from about 8% to about 15%, optimally between about 10% and 13% by weight.

Gelatin will be present in amount from about 0.00001% to about 5% preferably between about 0.0001% and 1%, optimally between about 0.0001% and 0.1% by weight. The form of gelatin may be as finely divided solid particles of average particle size ranging between about 1 and about 1000 microns, optimally between about 100 and about 400 microns.

Glycerin will be present to suspend the gelatin in amounts ranging from about 0.1% to about 10%, preferably between about 0.5% and 3%, optimally between about 1% and about 2% by weight.

Diglycerin may also be present in compositions of this invention. The amount may range from about 0.1% to about 10%, preferably between about 1% and about 2% by weight.

Conditioning agents may also be present in compositions of the invention. Such agents may be in the form of $C_8$-$C_{20}$ fatty acids or salts thereof. Typical fatty acids include lauric, myristic, oleic, stearic acids and mixtures thereof; preferably the acid or salt is based upon stearic acid. Typical fatty acid salts are those with cations such as sodium, potassium, diethanolammonium, triethanolammonium, ammonium ions and mixtures thereof. Conditioning agents will be present in an amount from about 0.01% to about 5%, preferably from about 0.05% to about 1% by weight of the total composition.

Optionally, there may be included within the compositions of the invention humectants which may be selected from propylene glycol, sorbitol and mixtures thereof. Amounts of these components may range from about 0.1% to about 10% by weight of the total composition.

Emollients such as fatty acid esters (e.g. glycol and diglycol stearate, glycerol stearate, cetyl acetate), mineral oil, silicone oil, lanolin and lanolin derivatives may be present in amounts from about 0.01% to about 3% by weight of the total composition.

Minor other functional components may also be present. These include acidulants such as citric acid, buffers, Vitamins A,D and E, panthenol and UV absorbers such as oxybenzone and ethylhexyl p-methoxycinnamate.

The following Examples will more fully illustrate the embodiments of this invention. All parts, percentages and proportions referred to herein and in the appended claims are by weight of the total composition unless otherwise stated.

EXAMPLE 1

A composition typical of the present invention was prepared whose formula is outlined in Table I.

TABLE I

| Ingredient | Weight % |
|---|---|
| Acetone | 85.0 |
| Glycerin | 1.5 |
| Diglycerin | 1.5 |
| Colorant | 0.2 |
| Fragrance | 0.2 |
| Gelatin | 0.0001 |
| Water | qs |

EXAMPLE 2

A composition typical of the present invention was prepared whose formula is outline in Table II.

TABLE II

| Ingredient | Weight % |
|---|---|
| Acetone | 85.0 |
| Glycerin | 1.5 |
| Diglcerin | 1.5 |
| Colorant | 0.4 |
| Fragrance | 0.2 |
| Citric Acid | 0.05 |
| Vitamin E Acetate | 0.01 |
| Gelatin | 0.0001 |
| Panthenol | 0.0001 |
| Water | qs |

EXAMPLE 3

A composition typical of the present invention was prepared whose formula is outlined in Table III.

TABLE III

| Ingredient | Weight % |
|---|---|
| Acetone | 85.0 |
| Glycerin | 1.5 |
| Diglycerin | 1.5 |
| Fragrance | 0.2 |
| UVINUL 400 ® | 0.2 |
| Colorant | 0.1 |
| Gelatin | 0.001 |
| Water | qs |

EXAMPLE 4

A composition typcial of the present invention can be prepared according to the formula outlined in Table IV.

TABLE IV

| Ingredient | Weight % |
|---|---|
| Acetone | 75.0 |
| Glycerin | 10.0 |
| Colorant | 0.2 |
| Fragrance | 0.2 |
| Gelatin | 1.0 |
| Water | qs |

EXAMPLE 5

A composition typical of the present invention can be prepared according to the formula outlined in Table V.

TABLE V

| Ingredient | Weight % |
|---|---|
| Acetone | 60.0 |
| Ethyl Acetate | 15.0 |
| Ethyl Alcohol | 5.0 |
| Glycerin | 5.0 |
| Gelatin | 0.1 |
| Water | qs |

EXAMPLE 6

A series of tests were conducted to determine the suspending ability by glycerin of gelatin particles.

(1) Centrifugation. To increase the force of gravity and accelerate the settling process formulations containing 85% acetone, 0.15% gelatin, water and either 0 or 1.5% glycerin were prepared. Each was spun for 10 minutes at an R.C.F. (relative centrifugal force) of 2,000. The container without the glycerin had a noticeably larger amount of settled gelatin.

(2) Viscosity. A HAAKE CV-20 Rheometer measured the viscosity of the two formulations containing 0.15% gelatin and either 0 or 1.5% glycerin. The temperature was 25° C. and the shear rate was 100 sec$^{-1}$. The viscosities were:

| PRODUCT | VISCOSITY @ 100 sec$^{-1}$, mPa-sec |
|---|---|
| 85% acetone/15% water | 0.463 |
| 85% acetone/13.5% water/1.5% glycerin | 0.622 |

The viscosity difference represents a 34.4% increase in the viscosity of the lacquer remover due to the addition of the glycerin. Thus, glycerin aids in the suspension of gelatin.

The foregoing description and Examples illustrate selected embodiments of the present invention and in light thereof various modifications will be suggested to one skilled in the art, all of which are in the spirit and purview of this invention.

What is claimed is:

1. A nail polish removing composition comprising:
   (i) from about 50% to about 99.5% of acetone;
   (ii) from about 0.00001% to about 5% by weight of gelatin;
   (iii) from about 0.1% to about 10% by weight of glycerin;
   (iv) from about 0.1% to about 25% by weight of water, and wherein the gelatin is stably suspended with the aid of glycerin in the acetone.

2. A composition according to claim 1 wherein gelatin is present in an amount from about 0.0001% to about 1% by weight.

3. A composition according to claim 1 wherein glycerin is present in an amount about 1% to about 5% by weight.

4. A composition according to claim 1 wherein the acetone is present in an amount from about 75% to about 90% by weight.

5. A composition according to claim 1 further comprising from about 0.1% to about 10% by weight of diglycerin.

* * * * *